(12) United States Patent
Schmitz et al.

(10) Patent No.: US 12,217,851 B2
(45) Date of Patent: Feb. 4, 2025

(54) IDENTIFICATION OF CANDIDATE SIGNS INDICATIVE OF AN NTRK ONCOGENIC FUSION

(71) Applicant: Bayer Consumer Care AG, Basel (CH)

(72) Inventors: Arndt Schmitz, Berlin (DE); Eren Metin Elci, Bensheim (DE); Faidra Stavropoulou, Berlin (DE); Mikhail Kachala, Cologne (DE); Antti Karlsson, Parainen (FI); Mikko Tukiainen, Kaarina (FI)

(*) Notice: Subject to any disclaimer, the term of this patent is extended or adjusted under 35 U.S.C. 154(b) by 455 days.

(21) Appl. No.: 17/595,191

(22) PCT Filed: Apr. 28, 2020

(86) PCT No.: PCT/EP2020/061665
§ 371 (c)(1),
(2) Date: Nov. 10, 2021

(87) PCT Pub. No.: WO2020/229152
PCT Pub. Date: Nov. 19, 2020

(65) Prior Publication Data
US 2022/0223261 A1   Jul. 14, 2022

(30) Foreign Application Priority Data
May 10, 2019   (EP) .................................... 19173832

(51) Int. Cl.
*G06T 7/00*   (2017.01)
*G06N 3/04*   (2023.01)
(Continued)

(52) U.S. Cl.
CPC .............. *G16H 30/40* (2018.01); *G06N 3/04* (2013.01); *G06T 7/0012* (2013.01);
(Continued)

(58) Field of Classification Search
CPC ........ G06V 20/698; G06T 2207/30004; G06T 7/0012

See application file for complete search history.

(56) References Cited

U.S. PATENT DOCUMENTS 9,922,421 B1 *   3/2018   Degani ................. G06T 7/0012
12,002,544 B2 *  6/2024   Lo ........................ C12Q 1/6869
(Continued)

FOREIGN PATENT DOCUMENTS

WO   2019084697 A1   5/2019

OTHER PUBLICATIONS

Safoora Deihimi et al, BRCA2, EGFR, and NTRK mutations in mismatch repair-deficient colorectal cancers with MSH2 or MLH1 mutations, 2017, Oncotarget vol. 8 (Year: 2017).*

(Continued)

*Primary Examiner* — Kevin Ky
(74) *Attorney, Agent, or Firm* — Morrison & Foerster LLP

(57) ABSTRACT

The present invention relates to the identification of one or more candidate signs indicative of an NTRK oncogenic fusion within patient data. Subject matter of the present invention are a computer-implemented method, a system, and a non-transitory computer-readable storage medium for determining a probability value from patient data associated with a subject patient, the probability value indicating the probability of the subject patient suffering from cancer caused by a mutation of a neurotrophic receptor tyrosine kinase (NTRK) gene.

3 Claims, 9 Drawing Sheets

(51) Int. Cl.
  *G06V 20/69* (2022.01)
  *G16H 10/40* (2018.01)
  *G16H 10/60* (2018.01)
  *G16H 30/40* (2018.01)
  *G16H 50/20* (2018.01)

(52) U.S. Cl.
  CPC ........... *G06V 20/698* (2022.01); *G16H 10/40* (2018.01); *G16H 10/60* (2018.01); *G16H 50/20* (2018.01); *G06T 2207/30004* (2013.01)

(56) References Cited

U.S. PATENT DOCUMENTS

| | | | |
|---|---|---|---|
| 2005/0262031 | A1 | 11/2005 | Saidi et al. |
| 2009/0252391 | A1* | 10/2009 | Matsuda ................ G16H 20/70 382/131 |
| 2017/0316567 | A1* | 11/2017 | Kotoku .................... G06T 7/11 |
| 2018/0130204 | A1* | 5/2018 | Degani ................ G06T 7/0012 |
| 2020/0327659 | A1* | 10/2020 | Sati ........................ G06V 10/82 |
| 2020/0342600 | A1* | 10/2020 | Sjöstrand ............... A61B 6/032 |

OTHER PUBLICATIONS

Arunachalam, H. B. et al., Apr. 17, 2019, "Viable and necrotic tumor assessment from whole slide images of osteosarcoma using machine-learning and deep-learning models," PLOS ONE, 14(4):e0210706.

Coudray, N. et al., Oct. 2018, "Classification and mutation prediction from non-small cell lung cancer histopathology images using deep learning," Nature Medicine, 24:1559-1567.

David, J. L. et al., 2018, "Infantile NTRK-associated Mesenchymal Tumors," Pediatric and Developmental Pathology, 21(1):68-78. no date available.

Extended European Search Report dated Nov. 18, 2019 for European Application No. 19173832.7, 11 pages.

Penault-Llorca, F. et al., May 9, 2019, "Testing algorithm for identification of patients with TRK fusion cancer," J Clin. Pathol., 72:460-467.

Davis, J. L. et al. (2017). "Infantile NTRK-associated Mesenchymal Tumors" Pediatric and Developmental Pathology, vol. 21(1), Jul. 6, 2017, pp. 68-78.

* cited by examiner

IDENTIFICATION OF CANDIDATE SIGNS INDICATIVE OF AN NTRK ONCOGENIC FUSION

CROSS REFERENCE TO RELATED APPLICATIONS

This application is a national stage application under 35 U.S.C. § 371 of International Application No. PCT/EP2020/062262, filed internationally on May 4, 2020, which claims the benefit of priority to European Application No. 19173592.7 filed May 9, 2019.

FIELD OF THE INVENTION

The present disclosure relates to the identification of one or more candidate signs indicative of an NTRK oncogenic fusion within patient data. Subject matter of the present invention are a computer-implemented method, a system, and a non-transitory computer-readable storage medium for determining a probability value from patient data associated with a subject patient, the probability value indicating the probability of the subject patient suffering from cancer caused by a mutation of a neurotrophic receptor tyrosine kinase (NTRK) gene.

BACKGROUND OF THE INVENTION

The tropomyosin receptor kinase (Trk) receptor family comprises three transmembrane proteins referred to as Trk A, B and C (TrkA, TrkB and TrkC) receptors, and are encoded by the NTRK1, NTRK2 and NTRK3 genes, respectively.

The wildtype forms of these receptor tyrosine kinases are expressed in human neuronal tissue, and play an essential role in both the physiology of development and function of the nervous system through activation by neurotrophins.

NTRK genes, similar to other genes, are subject to alterations, including fusions. Preclinical studies have demonstrated that Trk fusion proteins promote oncogenesis by mediating constitutive cell proliferation and survival.

NTRK oncogenic fusions arise from intra-chromosomal or inter-chromosomal rearrangements that juxtapose the kinase domain-containing 3' region of NTRK with the 5' region of NTRK's gene partner.

NTRK oncogenic fusions are infrequent but recurrent events observed in various types of congenital and acquired cancers (see e.g. Table 2 of Ed S. Kheder, David S. Hong: Emerging Targeted Therapy for Tumors with NTRK Fusion Proteins, clincancerres.aacrjournals.org, 2018, DOI: 10.1158/1078-0432.CCR-18-1156).

These genetic abnormalities have recently emerged as targets for cancer therapy, because novel compounds have been developed that are selective inhibitors of the constitutively active rearranged proteins. Over the past few years, various inhibitors targeting the Trk family members have been developed and tested in clinical trials (see e.g. Table 3 of Ed S. Kheder, David S. Hong: Emerging Targeted Therapy for Tumors with NTRK Fusion Proteins, clincancerres.aacrjournals.org, 2018, DOI: 10.1158/1078-0432.CCR-18-1156). Specifically, larotrectinib and entrectinib have emerged as potent, safe, and promising Trk inhibitors.

A major challenge in the development of these inhibitors and their use as therapeutics is the low incidence in each single tumor histology.

Next-generation sequencing provides a precise method to detect NTRK gene fusions (M. L. Metzker: Sequencing technologies—the next generation, Nat Rev Genet. 2010, 11(1), pages 31-46). However, performing gene analyses for each patient is expensive and, due to the low incidence of NTRK oncogenic fusions, inefficient.

Immunohistochemistry provides a routine method to detect protein expression of NTRK genes (for example, J. F. Hechtman et al.: Pan-Trk Immunohistochemistry Is an Efficient and Reliable Screen for the Detection of NTRK Fusions, Am J Surg Pathol. 2017, 41 (11), pages 1547-1551; https://www.prnewswire.com/news-releases/roche-launches-first-ivd-pan-trk-immunohistochemistry-assay-300755647.html). However, performing immunohistochemistry requires skills and the correlation between protein expression and gene fusion status is not trivial. Interpretation of IHC results requires the skills of a trained and certified medical professional pathologist. Similar practical challenges also hold true for other molecular assays such as FISH (fluorescence in situ hybridization) or PCR (polymerase chain reaction).

SUMMARY OF THE INVENTION

The subject matter of the present disclosure addresses the problem described above.

In some embodiments, a computer-implemented method for identifying one or more candidate signs indicative of an NTRK oncogenic fusion within patient data associated with a subject patient may comprise:
  receiving patient data of a subject patient suffering from cancer, the patient data comprising at least one histopathological image of tumor tissue of the subject patient;
  inputting the patient data into a prediction model trained via machine learning with a set of training data, the prediction model being configured for identifying within the patient data one or more characteristics of an NTRK oncogenic fusion;
  receiving as an output from the prediction model a probability value, the probability value indicating the probability of the subject patient suffering from cancer caused by an NTRK oncogenic fusion.

In some embodiments, a system may comprise:
a processor; and
a memory storing an application program configured to perform, when executed by the processor, an operation for identifying one or more candidate signs indicative of an NTRK oncogenic fusion within patient data associated with a subject patient, the operation comprising:
  receiving patient data of a subject patient suffering from cancer, the patient data comprising at least one histopathological image of tumor tissue of the subject patient;
  inputting the patient data into a prediction model trained via machine learning with a set of training data, the prediction model being configured for identifying within the patient data one or more characteristics of an NTRK oncogenic fusion;
  receiving as an output from the prediction model a probability value, the probability value indicating the probability of the subject patient suffering from cancer caused by an NTRK oncogenic fusion.

In some embodiments, a non-transitory computer-readable storage medium may comprise processor-executable instructions with which to perform an operation for identifying one or more candidate signs indicative of an NTRK oncogenic fusion within patient data associated with a subject patient, the operation comprising:

receiving patient data of a subject patient suffering from cancer, the patient data comprising at least one histopathological image of tumor tissue of the subject patient;

inputting the patient data into a prediction model trained via machine learning with a set of training data, the prediction model being configured for identifying within the patient data one or more characteristics of an NTRK oncogenic fusion;

receiving as an output from the prediction model a probability value, the probability value indicating the probability of the subject patient suffering from cancer caused by an NTRK oncogenic fusion.

The invention will be more particularly elucidated below without distinguishing between the subjects of the disclosure. On the contrary, the following elucidations are intended to apply analogously to all subjects of the disclosure, irrespective of in which context they occur.

The present disclosure serves to determine a probability value from patient data associated with a subject patient by means of a prediction model, the probability value indicating the probability of the subject patient suffering from cancer caused by a mutation of a neurotrophic receptor tyrosine kinase (NTRK) gene.

The term "mutation" refers herein to any gene alteration including DNA rearrangement, nucleotide(s) substitution, addition and/or deletion that results in expression of a tropomyosin receptor kinase (Trk) receptor possessing an altered amino acid sequence. In particular, the term refers to gene alteration that juxtapose the kinase domain-containing 3' region of NTRK (NTRK1, NTRK2, NTRK3) with the 5' region of a NTRK's gene partner.

NTRK gene family fusion partners and associated cancers can be found e.g. in Ed S. Kheder, David S. Hong: Emerging Targeted Therapy for Tumors with NTRK Fusion Proteins, clincancerres.aacrjournals.org, 2018, DOI: 10.1158/1078-0432.CCR-18-1156, the content of which is fully incorporated herein by reference (see in particular Table 1).

For the NTRK1 gene the following gene fusion partners in connection with colorectal cancers are described:
TPM3 (tropomyosin 3) (Ardini E, et al. The TPM3-NTRK1 rearrangement is a recurring event in colorectal carcinoma and is associated with tumor sensitivity to TRKA kinase inhibition. Mol Oncol. 2014; 8(8):1495-507),
LMNA (lamin A/C) (Sartore-Bianchi A et al. Sensitivity to Entrectinib Associated With a Novel LMNA-NTRK1 Gene Fusion in Metastatic Colorectal Cancer. J Natl Cancer Inst. 2016; 108(1)),
TPR (translocated promoter region) (Lee S J et al. NTRK1 rearrangement in colorectal cancer patients: evidence for actionable target using patient-derived tumor cell line. Oncotarget. 2015; 6(36):39028-35),
SCYL3, (SCY1 like pseudokinase 3) (Milione M., et al. Identification and characterization of a novel SCYL3-NTRK1 rearrangement in a colorectal cancer patient. Oncotarget. 2017; 8(33):55353-60.

For the NTRK1 gene the following gene fusion partners in connection with lung cancer are described:
CD74 (Vaishnavi A, et al. Oncogenic and drug-sensitive NTRK1 rearrangements in lung cancer. Nat Med. 2013; 19(11):1469-72),
MPRIP (myosin phosphatase rho interacting protein) (Vaishnavi A, et al. Oncogenic and drug-sensitive NTRK1 rearrangements in lung cancer. Nat Med. 2013; 19(11):1469-72),
SQSTM1 (sequestosome 1) (Farago A F, et al. Durable Clinical Response to Entrectinib in NTRK1-Rearranged Non-Small Cell Lung Cancer. J Thorac Oncol. 2015; 10(12):1670-4.).

For the NTRK2 gene the following gene fusion partners in connection with lung cancer are described:
TRIM24 (tripartite motif containing 24) (Stransky N, et al., The landscape of kinase fusions in cancer. Nat Commun. 2014; 5:4846).

For the NTRK1 gene the following gene fusion partners in connection with glioblastoma multiforme cancer are described:
ARHGEF2 (rho/rac guanine nucleotide exchange factor 2) (Zheng Z, et al. Anchored multiplex PCR for targeted next-generation sequencing. Nat Med. 2014; 20(12):1479-84.),
BCAN (brevican) (Kim J, et al. NTRK1 fusion in glioblastoma multiforme. PLoS One. 2014; 9(3):e91940.),
NFASC (neurofascin) (Frattini V, et al. The integrated landscape of driver genomic alterations in glioblastoma. Nat Genet. 2013; 45(10):1141-9.),
TPM3 (tropomyosin 3) (Wu G, et al. The genomic landscape of diffuse intrinsic pontine glioma and pediatric non-brainstem high-grade glioma. Nat Genet. 2014; 46(5):444-50.).

For the NTRK3 gene the following gene fusion partners in connection with glioblastoma multiforme cancer are described:
ETV6 (ets variant 6) (Zheng Z, et al. Anchored multiplex PCR for targeted next-generation sequencing. Nat Med. 2014; 20(12):1479-84. and Frattini V., et al. The integrated landscape of driver genomic alterations in glioblastoma. Nat Genet. 2013; 45(10):1141-9).

For the NTRK2 gene the following gene fusion partners in connection with pilocytic astrocytoma cancer are described:
NACC2 (NACC family member 2) (Jones D T, et al. Recurrent somatic alterations of FGFR1 and NTRK2 in pilocytic astrocytoma. Nat Genet. 2013; 45(8):927-32.),
QKI (KH domain containing RNA binding) (Jones D T, et al. Recurrent somatic alterations of FGFR1 and NTRK2 in pilocytic astrocytoma. Nat Genet. 2013; 45(8):927-32).

For the NTRK1 gene the following gene fusion partners in connection with spitzoid melanoma cancer are described:
TP53 (tumor protein P53) (Wiesner T, et al. Kinase fusions are frequent in Spitz tumours and spitzoid melanomas. Nat Commun. 2014; 5:3116.),
LMNA (lamin A/C) (Wiesner T, et al. Kinase fusions are frequent in Spitz tumours and spitzoid melanomas. Nat Commun. 2014; 5:3116).

For the NTRK1 gene the following gene fusion partners in connection with papillary thyroid cancer are described:
TPM3 (tropomyosin 3) (Bongarzone I, et al. High frequency of activation of tyrosine kinase oncogenes in human papillary thyroid carcinoma. Oncogene. 1989; 4(12):1457-62)),
TFG (TRK-fused gene) (Greco A, et al. The DNA rearrangement that generates the TRK-T3 oncogene involves a novel gene on chromosome 3 whose product has a potential coiled-coil domain. Mol Cell Biol. 1995; 15(11):6118-27.), TPR (translocated promoter region) (Greco A, et al., TRK-T1 is a novel oncogene formed by the fusion of TPR and TRK genes in human papillary thyroid carcinomas. Oncogene. 1992; 7(2):237-42.)).

For the NTRK3 gene the following gene fusion partners in connection with mammary analogue secretory carcinoma cancer are described:

ETV6 (ets variant 6) (Ito S, et al., Case report of Mammary Analog Secretory Carcinoma of the parotid gland. Pathol Int. 2012; 62(2):149-52., Del Castillo et al. Secretory Breast Carcinoma: A Histopathologic and Genomic Spectrum Characterized by a Joint Specific ETV6-NTRK3 Gene Fusion. Am J Surg Pathol. 2015; 39(11):1458-67).

For the NTRK3 gene the following gene fusion partners in connection with secretory breast carcinoma cancer are described:

ETV6 (ets variant 6) (Tognon C., et al. Expression of the ETV6-NTRK3 gene fusion as a primary event in human secretory breast carcinoma. Cancer Cell. 2002; 2(5):367-76).

For the NTRK1 gene the following gene fusion partners in connection with infantile fibrosarcoma cancer are described:

LMNA (lamin A/C) (Wong V., et al. Evaluation of a Congenital Infantile Fibrosarcoma by Comprehensive Genomic Profiling Reveals an LMNA-NTRK1 Gene Fusion Responsive to Crizotinib. J Natl Cancer Inst. 2016; 108(1)).

For the NTRK2 gene the following gene fusion partners in connection with head and neck squamous cell carcinoma cancer are described:

PAN3 (poly(A) specific ribonuclease subunit) (Stransky N, et al., landscape of kinase fusions in cancer. Nat Commun. 2014; 5:4846.).

For the NTRK3 gene the following gene fusion partners in connection with mesoblastic nephroma cancer are described:

ETV6 (ets variant 6) (Anderson J, et al., Expression of ETV6-NTRK in classical, cellular and mixed subtypes of congenital mesoblastic nephroma. Histopathology. 2006; 48(6):748-53).

For the NTRK3 gene the following gene fusion partners in connection with gastrointestinal stromal tumor cancer are described:

ETV6 (ets variant 6) (Brenca M, et al. Transcriptome sequencing identifies ETV6-NTRK3 as a gene fusion involved in GIST. J Pathol. 2016; 238(4):543-9., Shi E, et al. FGFR1 and NTRK3 actionable alterations in "Wild-Type" gastrointestinal stromal tumors. J Transl Med. 2016; 14(1):339).

The probability value, indicating the probability of the cancer being caused by a mutation of a neurotrophic receptor tyrosine kinase (NTRK) gene, is determined from patient data. The patient data comprise at least one histopathological image of tumor tissue of the subject patient.

The at least one histopathological image can be obtained from the subject patient by biopsy.

In some embodiments of the present disclosure, the at least one histopathological image may be a microscopic image of tumor tissue of the subject patient. The magnification factor is preferably in the range of 10 to 60, more preferably in the range of 20 to 40, whereas a magnification factor of e.g. "20" means that a distance of 0.05 mm in the tumor tissue corresponds to a distance of 1 mm in the image (0.05 mm×20=1 mm).

In some embodiments of the present disclosure, the at least one histopathological image may be a whole-slide image.

In some embodiments of the present disclosure, the at least one histopathological image may be an image of a stained tumor tissue sample. One or more dyes can be used to create the stained images. Preferred dyes may include hematoxylin and eosin.

In some embodiments of the present disclosure, the at least one histopathological image may be a whole-slide image from a histopathological tissue slide of a stained tumor tissue sample.

Methods for creating histopathological images, in particular stained whole-slide microscopy images, are extensively described in scientific literature and textbooks (see e.g. S. K. Suvarna et al.: Bancroft's Theory and Practice of Histological Techniques, 8th Ed., Elsevier 2019, ISBN 978-0-7020-6864-5; A. F. Frangi et al.: Medical Image Computing and Computer Assisted Intervention—MICCAI 2018, 21st International Conference Granada, Spain, 2018 Proceedings, Part II, ISBN 978-030-00933-5; L. C. Junqueira et al.: Histologic, Springer 2001, ISBN: 978-354-041858-0; N. Coudray et al.: Classification and mutation prediction from non-small cell lung cancer histopathology images using deep learning, Nature Medicine, Vol. 24, 2018, pages 1559-1567) the content of which is fully incorporated into this specification by reference.

The at least one histopathological image may be a digital image. A digital image is a numeric representation, normally binary, of a two-dimensional image Depending on whether the image resolution is fixed, it may be of vector or raster type. In a preferred embodiment of the present invention, the at least one histopathological image is a raster image holding RGB color values in 3 image channels. The RGB color model is an additive color model in which red (R), green (G) and blue (B) are added together in various ways to reproduce a broad array of colors. Alternatively, the at least one histopathological image is in Color Space Pixel (YUV) format having brightness, luminance, and color chrominance values. Other formats are conceivable as well.

Preferably the number of recorded pixels (pixel resolution) of the at least one histopathological image is in the range of 1,000×1,000 pixels to 500,000×500,000 pixels, more preferably in the range of 10,000×10,000 pixels to 100,000 to 100,000 pixels. The image can be quadratic or rectangular or of any other shape.

In some embodiments, the patient data may comprise more than one histopathological image. The histopathological images can be obtained e.g. at different magnifications (see e.g. WO2018/156133, the content of which is fully incorporated herein by reference).

In some embodiments, the at least one histopathological image may be segmented into tumor regions and healthy regions. Tumor regions show tumor tissue. Healthy regions show healthy tissue. The segmentation may be done automatically using a trained convolutional neural network (see e.g. N. Coudray: Classification and mutation prediction from non-small cell lung cancer histopathology images using deep learning, Nature Medicine Vol 24, 1560, 2018, pages 1559-1567).

Depending on the sizes of the histopathological images used for training and validation of the prediction model as well as for prediction purposes on the one hand side, and the available computer power on the other hand side, the images can be divided into smaller preferably non-overlapping tiles. Training and validation of the prediction model as well as predictions of probability values may then preferably performed using tiles instead of the whole image. Preferably only those tiles are used which show tumor regions.

Additional patient data which can be used for the prediction of the probability value are include anatomic or physiology data of the patient, such as information about patient's height and weight, gender, age, vital parameters (such as blood pressure, breathing frequency and heart rate), tumor grades, ICD-9 classification, oxygenation of tumor, degree of metastasis of tumor, blood count value tumor indicator value like PA value, information about the tissue the histopathological image is created from (e.g. tissue type, organ), further symptoms, medical history etc. In some embodiments, the pathology report of the histopathological images can be used for the prediction of the probability value, using text mining approaches. In some embodiments, a next generation sequencing raw data set which does not cover the TRK genes' sequences can be used for the prediction of the probability value.

In some embodiments, patient data can be e.g. collected from one or more databases or inputted into the system according to the present disclosure manually by a user.

In some embodiments, the patient data may be inputted into a prediction model. The prediction model may use one or more machine learning algorithms. A machine learning algorithm is an algorithm that can learn based on a set of training data. Embodiments of machine learning algorithms can be designed to model high-level abstractions within a data set. For example, image recognition algorithms can be used to determine which of several categories to which a given input belong; regression algorithms can output a numerical value given an input.

In some embodiments, the prediction model can be or comprise an artificial neural network. The present invention may use an artificial neural network comprising at least three layers of processing elements: a first layer with input neurons (nodes), an Nth layer with at least one output neuron (node), and N-2 inner layers, where N is a natural number greater than 2.

In such a network, the output neuron(s) may serve(s) to predict at least one probability value, the probability value indicating the probability of the subject patient suffering from cancer caused by an NTRK oncogenic fusion. The input neurons may serve to receive patient data as input values. In some embodiments, there may be one input neuron for each pixel of the at least one histopathological image. There can be additional input neurons for the additional patient data as listed above.

The processing elements of the layers may be interconnected in a predetermined pattern with predetermined connection weights between the processing elements. In some embodiments, the network may have been previously trained to identify one or more candidate signs indicative of an NTRK oncogenic fusion within the patient data. The training may be performed with a set of training data comprising patient data for which candidate signs indicative of an NTRK oncogenic fusion have been verified or excluded by means of further medical investigations such as genetic analysis of the tumor tissue.

When trained, the connection weights between the processing elements may contain information regarding the relationship between the patient data (input) and the probability value (output), which can be used to predict the probability value for a new subject patient on the basis of his/her patient data.

In some embodiments, each network node may represent a simple calculation of the weighted sum of inputs from prior nodes and a non-linear output function. The combined calculation of the network nodes may relate the inputs to the output(s).

In some embodiments, separate networks can be developed for each property measurement or groups of properties can be included in a single network. Preferably, different dimensions of the patient data are combined at the end of the algorithm.

In some embodiments, training may estimate network weights that may allow the network to calculate (an) output value(s) close to the measured output value(s). A supervised training method can be used in which the output data is used to direct the training of the network weights. The network weights may be initialized with small random values or with the weights of a prior partially trained network. The training data inputs may be applied to the network and the output values may be calculated for each training sample. The network output values may be compared to the measured output values. A backpropagation algorithm may be applied to correct the weight values in directions that reduce the error between measurd and calculated outputs. The process may be iterated until no further reduction in error can be made or until a predefined prediction accuracy has been reached.

In some embodiments, a cross-validation method can be employed to split the data into training and validation data sets. The training data set may be used in the backpropagation training of the network weights. The validation data set may be used to verify that the trained network generalizes to make good predictions. In some embodiments, the best network weight set can be taken as the one that best predicts the outputs of the test data set. Similarly, varying the number of network hidden nodes and determining the network that performs best with the data sets optimizes the number of hidden nodes.

In some embodiments, forward prediction may use the trained network to calculate a probability value indicating the probability of a patient suffering from cancer caused by an NTRK oncogenic fusion. Patient data may be inputted into the trained network. A feed forward calculation through the network may be made to predict the output property value(s). The predicted measurements can be compared to (a) property target value(s) or tolerance(s). Since the method of the disclosure may be based on historical data of property values, the prediction of property values using such method typically have an error approaching the error of the empirical data, so that the predictions are often just as accurate as verification experiments.

In a some embodiments of the present disclosure, the prediction model may be or may comprise a convolutional neural network (CNN).

A CNN is a class of deep neural networks, most commonly applied to analyzing visual imagery. A CNN comprises an input layer with input neurons, an output layer with at least one output neuron, as well as multiple hidden layers between the input layer and the output layer.

The hidden layers of a CNN typically consist of convolutional layers, ReLU (Rectified Linear Units) layer i.e. activation function, pooling layers, fully connected layers and normalization layers.

The nodes in the CNN input layer are organized into a set of "filters" (feature detectors), and the output of each set of filters is propagated to nodes in successive layers of the network. The computations for a CNN include applying the convolution mathematical operation to each filter to produce the output of that filter. Convolution is a specialized kind of mathematical operation performed by two functions to produce a third function that is a modified version of one of the two original functions. In convolutional network terminology, the first function to the convolution can be referred to as the input, while the second function can be referred to as the convolution kernel. The output may be referred to as the feature map. For example, the input to a convolution layer can be a multidimensional array of data that defines the various color components of an input image. The convolution kernel can be a multidimensional array of parameters, where the parameters are adapted by the training process for the neural network.

By analysis of the CNN, one can reveal patterns in the data which are not obvious and were used preferred (i.e., weighted more strongly) by the CNN while analyzing the training data. This explainable AI approach helps to generate trust in the performance of the prediction model.

In some embodiments, the systems and methods of the present disclosure can be used to
  a) detect NTRK fusion events in other indications than in those being trained on (i.e., an algorithm trained on thyroid data sets is useful in lung cancer data sets)
  b) detect NTRK fusion events involving other TRK family members (i.e., an algorithm trained on NTRK1, NTRK3 fusions is useful to predict also NTRK2 fusions)
  c) detect NTRK fusion events involving other fusion partners (i.e., an algorithm trained on LMNA-fusion data sets is useful also in TPM3-fusion data sets)
  d) discover novel fusion partners (i.e., an algorithm trained on known fusion events might predict a fusion in a new data set which is then confirmed via molecular assay to involve a not yet described fusion partner of a NTRK family member).

The prediction model may generate a probability value indicating the probability of a patient suffering from cancer caused by an NTRK oncogenic fusion. The probability value can be outputted to a user and/or stored in a database. In some embodiments, the probability value can be a real number in the range from 0 to 1, whereas a probability value of 0 means that it is impossible that the cancer is caused by an NTRK oncogenic fusion, and a probability value of 1 means that there is no doubt that the cancer is caused by an NTRK oncogenic fusion. In some embodiments, the probability value can also be expressed by a percentage.

In some embodiments of the present disclosure, the probability value may be compared with a predefined threshold value. In the event the probability value is lower than the threshold value, the probability that the patient suffers from cancer caused by an NTRK oncogenic fusion is low; treating the patient with a Trk inhibitor is not indicated; further investigations are required in order to determine the cause of cancer. In the event the probability value equals the threshold value or is greater than the threshold value, it is reasonable to assume that the cancer is caused by an NTRK oncogenic fusion; the treatment of the patient with a Trk inhibitor can be indicated; further investigations to verify the assumption can be initiated (e.g. performing a genetic analysis of the tumor tissue).

In some embodiments, the threshold value can be a value between 0.5 and 0.99999999999, e.g. 0.8 (80%) or 0.81 (81%) or 0.82 (82%) or 0.83 (83%) or 0.84 (84%) or 0.85 (85%) or 0.86 (86%) or 0.87 (87%) or 0.88 (88%) or 0.89 (89%) or 0.9 (90%) or 0.91 (91%) or 0.92 (92%) or 0.93 (93%) or 0.94 (94%) or 0.95 (95%) or 0.96 (96%) or 0.97 (97%) or 0.98 (98%) or 0.99 (99%) or any other value (percentage).

In some embodiments, the prediction model can also perform a classification. On the basis of the input data, the at least one histopathological image may be assigned to one of at least two classes, a first class and a second class. The first class may comprise images showing tumor tissue wherein the tumor is caused by an NTRK oncogenic fusion. The second class may comprise images which do not show tumor tissue caused by an NTRK oncogenic fusion. In this case, the probability value represents the class the respective histopathological image is assigned to.

In some embodiments, the present disclosure may relate to the use of a Trk inhibitor in the manufacture of a medicament for treating cancer in a subject patient, wherein the subject patient who shall be treated may be one for whom a probability value is determined which may be equal to or greater than a predefined threshold value, the probability value indicating the probability of a patient suffering from cancer caused by an NTRK oncogenic fusion, the probability value being determined by means of a prediction model on the basis of patient data.

In some embodiments, the present disclosure may relate to a Trk inhibitor for use in treating cancer in a subject patient, wherein the subject patient who shall be treated may be one for whom a probability value is determined which may be equal to or greater than a predefined threshold value, the probability value indicating the probability of a patient suffering from cancer caused by an NTRK oncogenic fusion, the probability value being determined by means of a prediction model on the basis of patient data.

In some embodiments, the present disclosure may relate to a Trk inhibitor for use in a method of treatment of cancer in a subject patient, wherein the subject patient who shall be treated may be one for whom a probability value is determined which may be equal to or greater than a predefined threshold value, the probability value indicating the probability of a patient suffering from cancer caused by an NTRK oncogenic fusion, the probability value being determined by means of a prediction model on the basis of patient data.

In some embodiments, the present disclosure may relate to the use of a Trk inhibitor for the treatment of cancer in a subject patient, wherein the subject patient who shall be treated may be one for whom a probability value is determined which may be equal to or greater than a predefined threshold value, the probability value indicating the probability of a patient suffering from cancer caused by an NTRK oncogenic fusion, the probability value being determined by means of a prediction model on the basis of patient data.

In some embodiments, the present disclosure may relate to a method for identifying a subject patient disposed to respond favorably to a Trk inhibitor for treating cancer. The method may comprise the following steps:
  receiving patient data of the subject patient, the patient data comprising at least one histopathological image of tumor tissue of the subject patient;
  inputting the patient data into a prediction model trained via machine learning with a set of training data, the prediction model being configured for identifying within the patient data one or more characteristics of an NTRK oncogenic fusion;
  receiving as an output from the prediction model a probability value, the probability value indicating the probability of the subject patient suffering from cancer caused by an NTRK oncogenic fusion;
  comparing the probability value with a predefined threshold value;

wherein the probability value is equal to or greater than the predefined threshold value.

In some embodiments, the present disclosure may relate to a method of treating cancer in a subject patient. The method may comprise the following steps:
- receiving patient data of the subject patient, the patient data comprising at least one histopathological image of tumor tissue of the subject patient;
- inputting the patient data into a prediction model trained via machine learning with a set of training data, the prediction model being configured for identifying within the patient data one or more characteristics of an NTRK oncogenic fusion;
- receiving as an output from the prediction model a probability value, the probability value indicating the probability of the subject patient suffering from cancer caused by an NTRK oncogenic fusion;
- comparing the probability value with a predefined threshold value whereas the probability value is equal to or greater than the predefined threshold value;
- administering a therapeutically effective amount of a Trk inhibitor.

In some embodiments, the present disclosure may relate to a kit. The kit may comprise:
- a medicament comprising a Trk inhibitor, and
- a computer program product, the computer program product comprising a non-transitory computer-readable storage medium comprising processor-executable instructions with which to perform an operation for identifying one or more candidate signs indicative of an NTRK oncogenic fusion within patient data associated with a subject patient, the operation comprising:
  - receiving patient data of a subject patient suffering from cancer, the patient data comprising at least one histopathological image of tumor tissue of the subject patient;
  - inputting the patient data into a prediction model trained via machine learning with a set of training data, the prediction model being configured for identifying within the patient data one or more characteristics of an NTRK oncogenic fusion;
  - receiving as an output from the prediction model a probability value, the probability value indicating the probability of the subject patient suffering from cancer caused by an NTRK oncogenic fusion;
  - comparing the probability value with a predefined threshold value whereas the probability value is equal to or greater than the predefined threshold value.

In some embodiments, the Trk inhibitor is Sitravatinib, Belizatinib, Entrectinib or Larotrectinib.

Sitravatinib (MGCD-516) is a small-molecule multi-kinase inhibitor that targets MET, AXL, MER, as well as members of the vascular endothelial growth factor receptor (VEGFR), platelet-derived growth factor receptor (PDGFR), discoidin domain receptor tyrosine kinase 2 (DDR2), and Trk families.

Belizatinib (TSR-011) is an oral dual ALK and pan-Trk inhibitor.

Entrectinib (N-[5-(3,5-Difluorobenzyl)-1H-indazol-3-yl]-4-(4-methyl-1-piperazinyl)-2-(tetrahydro-2H-pyran-4-ylamino)benzamide) is a an oral ATP-competitive, pan-Trk, ROS1, and ALK Trk inhibitor.

Larotrectinib ((3S)—N-{5-[(2R)-2-(2,5-difluorophenyl)pyrrolidin-1-yl]pyrazolo[1,5-a]pyrimidin-3-yl-}-3-hydroxy-pyrrolidine-1-carboxamide) is an orally administered selective tropomyosin receptor kinases (Trk) inhibitor which can be used for the treatment of genomically defined cancers harbouring NTRK gene fusions including solid tumours, non-Hodgkin lymphoma, histiocytic disorders and primary CNS cancers. Preclinical development is underway for precursor cell lymphoblastic leukaemia-lymphoma (acute lymphoblastic leukaemia) in the US.

In some embodiments, the Trk inhibitor is Larotrectinib.

In some embodiments of the present invention, the cancer may be selected from: lung cancer, colorectal cancer, papillary thyroid cancer, glioblastoma multiforme, sarcoma, secretory breast cancer, mammary analog secretory carcinoma, non-Hodgkin lymphoma, histiocytic disorders and primary CNS (central nervous system) cancer.

In some embodiments, the present disclosure may relate to a system. The system may comprise
- an input unit,
- a processing unit and
- an output unit, wherein the input unit is configured to accept patient data of a subject patient, the patient data comprising at least one histopathological image of tumor tissue of the subject patient;

wherein the processing unit is configured to determine, on the basis of the patient data, a probability value, the probability value indicating the probability of the subject patient suffering from cancer caused by an NTRK oncogenic fusion;

wherein the processing unit is optionally configured to compare the probability value with a predefined threshold value and thereby determining a comparison result;

wherein the output unit is configured to display the probability value and/or to display the comparison result.

The operations in accordance with the teachings herein may be performed by at least one computer specially constructed for the desired purposes or general purpose computer specially configured for the desired purpose by at least one computer program stored in a typically non-transitory computer readable storage medium.

The term "non-transitory" is used herein to exclude transitory, propagating signals or waves, but to otherwise include any volatile or non-volatile computer memory technology suitable to the application.

The term "computer" should be broadly construed to cover any kind of electronic device with data processing capabilities, including, by way of non-limiting example, personal computers, servers, embedded cores, computing system, communication devices, processors (e.g. digital signal processor (DSP)), microcontrollers, field programmable gate array (FPGA), application specific integrated circuit (ASIC), etc.) and other electronic computing devices.

The term "process" as used above is intended to include any type of computation or manipulation or transformation of data represented as physical, e.g. electronic, phenomena which may occur or reside e.g. within registers and/or memories of at least one computer or processor. The term processor includes a single processing unit or a plurality of distributed or remote such units.

Any suitable processor/s, display and input means may be used to process, display e.g. on a computer screen or other computer output device, store, and accept information such as information used by or generated by any of the methods and system shown and described herein; the above processor/s, display and input means including computer programs, in accordance with some or all of the embodiments of the present invention. Any or all functionalities of the invention shown and described herein, such as but not limited to operations within flowcharts, may be performed by any one or more of: at least one conventional personal computer processor, workstation or other programmable device or computer or electronic computing device or processor, either general-purpose or specifically constructed, used for processing; a computer display screen and/or printer and/or speaker for displaying; machine-readable memory such as optical disks, CDROMs, DVDs, BluRays, magnetic-optical discs or other discs; RAMs, ROMs, EPROMs, EEPROMs, magnetic or optical or other cards, for storing, and keyboard or mouse for accepting. Modules shown and described herein may include any one or combination or plurality of: a server, a data processor, a memory/computer storage, a communication interface, a computer program stored in memory/computer storage.

Any suitable input device, such as but not limited to a camera sensor, may be used to generate or otherwise provide information received by the system and methods shown and described herein. Any suitable output device or display may be used to display or output information generated by the system and methods shown and described herein. Any suitable processor/s may be employed to compute or generate information as described herein and/or to perform functionalities described herein and/or to implement any engine, interface or other system described herein. Any suitable computerized data storage e.g. computer memory may be used to store information received by or generated by the systems shown and described herein. Functionalities shown and described herein may be divided between a server computer and a plurality of client computers. These or any other computerized components shown and described herein may communicate between themselves via a suitable computer network.

A system which is particularly suitable for executing the operation/steps/methods of the presentation invention is disclosed in WO2018/184194A the content of which is incorporated herein by reference.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. As used herein, for example, the singular forms "a", "an", "the" and the like include plural referents unless the context clearly dictates otherwise. The terms "data", "information", "content" and similar terms may be used interchangeably, according to some example implementations of the present invention, to refer to data capable of being transmitted, received, operated on, and/or stored. Also, for example, reference may be made herein to quantitative measures, values, relationships or the like. Unless otherwise stated, any one or more if not all of these may be absolute or approximate to account for acceptable variations that may occur, such as those due to engineering tolerances or the like. Like reference numerals refer to like elements throughout.

BRIEF DESCRIPTION OF THE DRAWINGS

FIG. 10 (b) illustrates an output of the prediction tool, according to some embodiments.

FIG. 10 (c) illustrates a digital image of an adjacent FFPE tumor tissue section stained with an antibody for indicating presence of TRK proteins using immunohistochemistry.

DETAILED DESCRIPTION OF EXEMPLARY EMBODIMENTS

Figure 1:
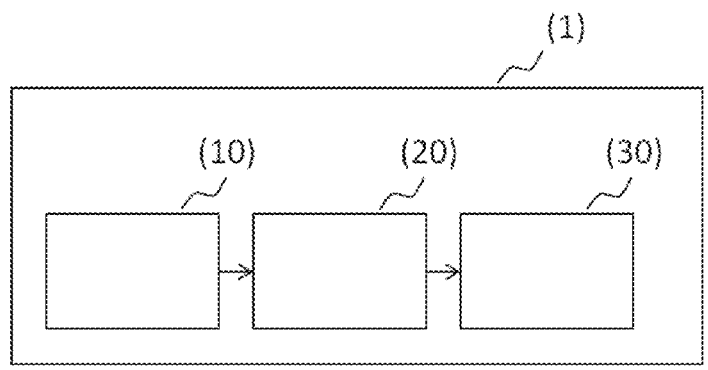
FIG. 1 shows a system for determining a probability value from patient data, according to some embodiments.

FIG. 1 shows schematically a system 1 for determining a probability value from patient data, according to some embodiments. As shown, system 1 comprises an input component 10, a processor 20, and an output component 30. In some embodiments, the input component 10 may accept patient data and may forward the patient data to the processor 20 (depicted by the arrow between the input component 10 and the processor 20). The processor 20 may determine a probability value based on the patient data. In some embodiments, the processor may be optionally configured to compare the probability value with a predefined threshold value and thereby determining a comparison result. The probability value and/or the comparison result may be transmitted from the processor 20 to the output component 30 (depicted by the arrow between the processor 20 and the output component 30). In some embodiments, output component 30 may display the probability value and/or the comparison result. The input component 10, the processor 20 and the output component 30 can be components of one or more computer systems.

Figure 2:
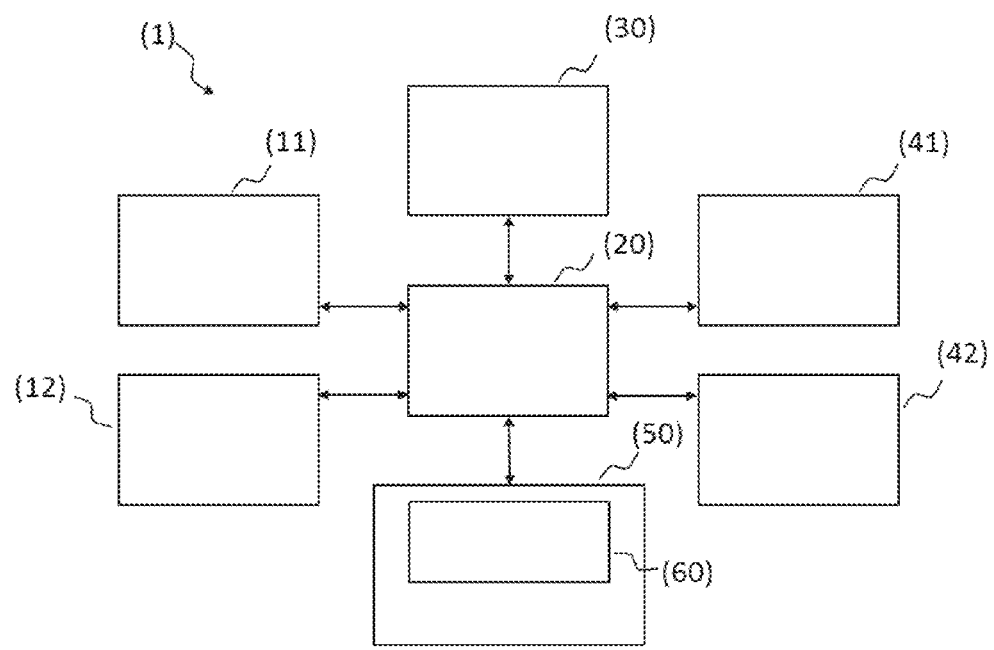
FIG. 2 shows a detailed schematic of a system for determining a probability value from patient data, according to some embodiments.

FIG. 2 shows a detailed schematic of a computer system 1 for determining a probability value from patient data, according to some embodiments of the present disclosure. Generally, a computer system of exemplary implementations of the present disclosure may be referred to as a computer and may comprise, include, or be embodied in one or more fixed or portable electronic devices. The computer may include one or more of each of a number of components such as, for example, the processor 20 connected to a memory 50 (e.g., storage device).

In some embodiments, the processor 20 may be composed of one or more processors alone or in combination with one or more memories. The processor 20 may generally be any piece of computer hardware that is capable of processing information such as, for example, data, computer programs, and/or other suitable electronic information. The processor 20 may be composed of a collection of electronic circuits some of which may be packaged as an integrated circuit or multiple interconnected integrated circuits (an integrated circuit at times more commonly referred to as a "chip"). The processor 20 may be configured to execute computer programs, which may be stored onboard the processor 20 or otherwise stored in the memory 50 of the same or another computer.

The processor 20 may be a number of processors, a multi-core processor, or some other type of processor, depending on the particular implementation. Further, the processor 20 may be implemented using a number of heterogeneous processor systems in which a main processor is present with one or more secondary processors on a single chip. In some embodiments, the processor 20 may be a symmetric multi-processor system containing multiple processors of the same type. In some embodiments, the processor 20 may be embodied as or otherwise include one or more ASICs, FPGAs, or the like. Thus, although the processor 20 may be capable of executing a computer program to perform one or more functions, the processor 20 of various embodiments may be capable of performing one or more functions without the aid of a computer program. In either instance, the processor 20 may be appropriately programmed to perform functions or operations according to example embodiments of the present disclosure.

The memory 50 may generally be any piece of computer hardware that is capable of storing information such as, for example, data, computer programs (e.g., computer-readable program code 60), and/or other suitable information either on a temporary basis and/or a permanent basis. The memory may include volatile and/or non-volatile memory, and may be fixed or removable. Examples of suitable memory include random access memory (RAM), read-only memory (ROM), a hard drive, a flash memory, a thumb drive, a removable computer diskette, an optical disk, a magnetic tape or some combination of the above. Optical disks may include compact disk-read only memory (CD-ROM), compact disk-read/write (CD-R/W), DVD, Blu-ray disk or the like. In various instances, the memory may be referred to as a computer-readable storage medium. The computer-readable storage medium is a non-transitory device capable of storing information, and is distinguishable from computer-readable transmission media such as electronic transitory signals capable of carrying information from one location to another. Computer-readable medium as described herein may generally refer to a computer-readable storage medium or computer-readable transmission medium.

In addition to the memory 50, the processing unit 20 may also be connected to one or more interfaces for displaying, transmitting and/or receiving information. The interfaces may include one or more communications interfaces and/or one or more user interfaces. The communications interface(s) may be configured to transmit and/or receive information, such as to and/or from other computer(s), network(s), database(s) or the like. The communications interface may be configured to transmit and/or receive information by physical (wired) and/or wireless communications links. The communications interface(s) may include interface(s) 41 to connect to a network, such as using technologies such as cellular telephone, Wi-Fi, satellite, cable, digital subscriber line (DSL), fiber optics, and the like. In some embodiments, the communications interface(s) may include one or more short-range communications interfaces 42 configured to connect devices using short-range communications technologies such as NFC, RFID, Bluetooth, Bluetooth LE, ZigBee, infrared (e.g., IrDA) or the like.

The user interfaces may include a display 30. The display may be configured to present or otherwise display information to a user, suitable examples of which include a liquid crystal display (LCD), light-emitting diode display (LED), plasma display panel (PDP), or the like. The user input interface(s) 11 may be wired or wireless, and may be configured to receive information from a user into the computer system 1, such as for processing, storage, and/or display. Suitable examples of user input interfaces include a microphone, image or video capture device, keyboard or keypad, joystick, touch-sensitive surface (separate from or integrated into a touchscreen) or the like. In some embodiments, the user interfaces may include automatic identification and data capture (AIDC) technology 12 for machine-readable information. This may include barcode, radio frequency identification (RFID), magnetic stripes, optical character recognition (OCR), integrated circuit card (ICC), and the like. The user interfaces may further include one or more interfaces for communicating with peripherals such as printers and the like.

As indicated above, program code instructions may be stored in memory and executed by a processor that is programmed to implement functions of the systems, subsystems, tools, and their respective elements described herein. As will be appreciated, any suitable program code instructions may be loaded onto a computer or other programmable apparatus from a computer-readable storage medium to produce a particular machine, such that the particular machine becomes a means for implementing the functions specified herein. These program code instructions may also be stored in a computer-readable storage medium that can direct a computer, processor, or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into a computer, processor, or other programmable apparatus to configure the computer, processor, or other programmable apparatus to execute operations to be performed on or by the computer, processor, or other programmable apparatus.

Retrieval, loading, and execution of the program code instructions may be performed sequentially such that one instruction is retrieved, loaded, and executed at a time. In some embodiments, retrieval, loading, and/or execution may be performed in parallel such that multiple instructions are retrieved, loaded, and/or executed together. Execution of the program code instructions may produce a computer-implemented process such that the instructions executed by the computer, processing circuitry or other programmable apparatus provide operations for implementing functions described herein.

Execution of instructions by a processor, or storage of instructions in a computer-readable storage medium, supports combinations of operations for performing the specified functions. In this manner, a computer system 1 may include a processor 20 and a computer-readable storage medium or memory 50 coupled to the processing circuitry, where the processing circuitry is configured to execute computer-readable program code 60 stored in the memory. It will also be understood that one or more functions, and combinations of functions, may be implemented by special purpose hardware-based computer systems and/or processing circuitry which perform the specified functions, or combinations of special purpose hardware and program code instructions.

Figure 3:
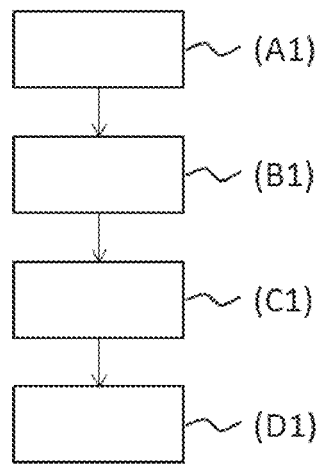
FIG. 3 shows a method for determining a probability value, according to some embodiments.

FIG. 3 shows a method for determining a probability value, according to some embodiments.

As shown, the method steps may comprise:
(A1) receiving patient data of a subject patient suffering from cancer, the patient data comprising at least one histopathological image of tumor tissue of the subject patient;
(B1) inputting the patient data into a prediction model trained via machine learning with a set of training data;
(C1) obtaining from the prediction model a probability value, the probability value indicating the probability of the subject patient suffering from cancer caused by an NTRK oncogenic fusion;
(D1) outputting and/or storing the probability value.

Figure 4:
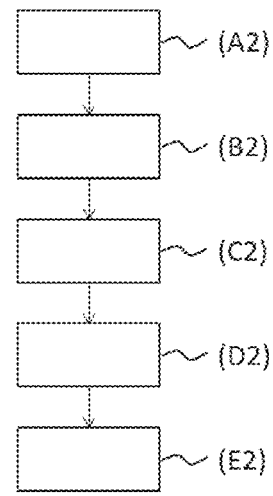
FIG. 4 shows a method for determining a probability value, according to some embodiments.

FIG. 4 shows a method for determining a probability value, according to some embodiments.

As shown, the method steps may comprise:
(A2) receiving patient data of a subject patient suffering from cancer, the patient data comprising at least one histopathological image of tumor tissue of the subject patient;
(B2) inputting the patient data into a prediction model trained via machine learning with a set of training data;
(C2) obtaining from the prediction model a probability value, the probability value indicating the probability of the subject patient suffering from cancer caused by an NTRK oncogenic fusion;
(D2) comparing the probability value with a predefined threshold value and thereby determining a comparison result;
(E2) outputting and/or storing the probability value and/or the comparison result.

Figure 5:
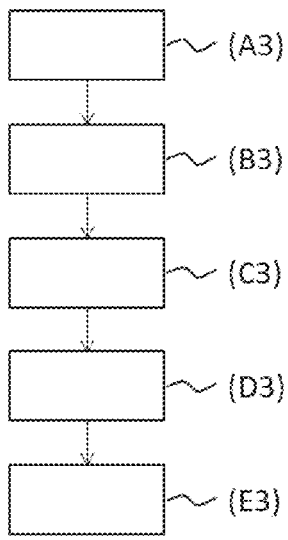
FIG. 5 shows a method for determining a probability value, according to some embodiments.

FIG. 5 shows a method for determining a probability value, according to some embodiments.

As shown, the method steps may comprise:
(A3) receiving patient data of a subject patient suffering from cancer, the patient data comprising at least one histopathological image of tumor tissue of the subject patient;
(B3) inputting the patient data into a prediction model trained via machine learning with a set of training data;
(C3) obtaining from the prediction model a probability value, the probability value indicating the probability of the subject patient suffering from cancer caused by an NTRK oncogenic fusion;
(D3) comparing the probability value with a predefined threshold value;
(E3) in the event that the probability value is equal to or greater than the threshold value: initiating further investigations for verification of the indication that the subject patient suffers from cancer caused by an NTRK oncogenic fusion or administering a therapeutically effect amount of a Trk inhibitor.

Figure 6:
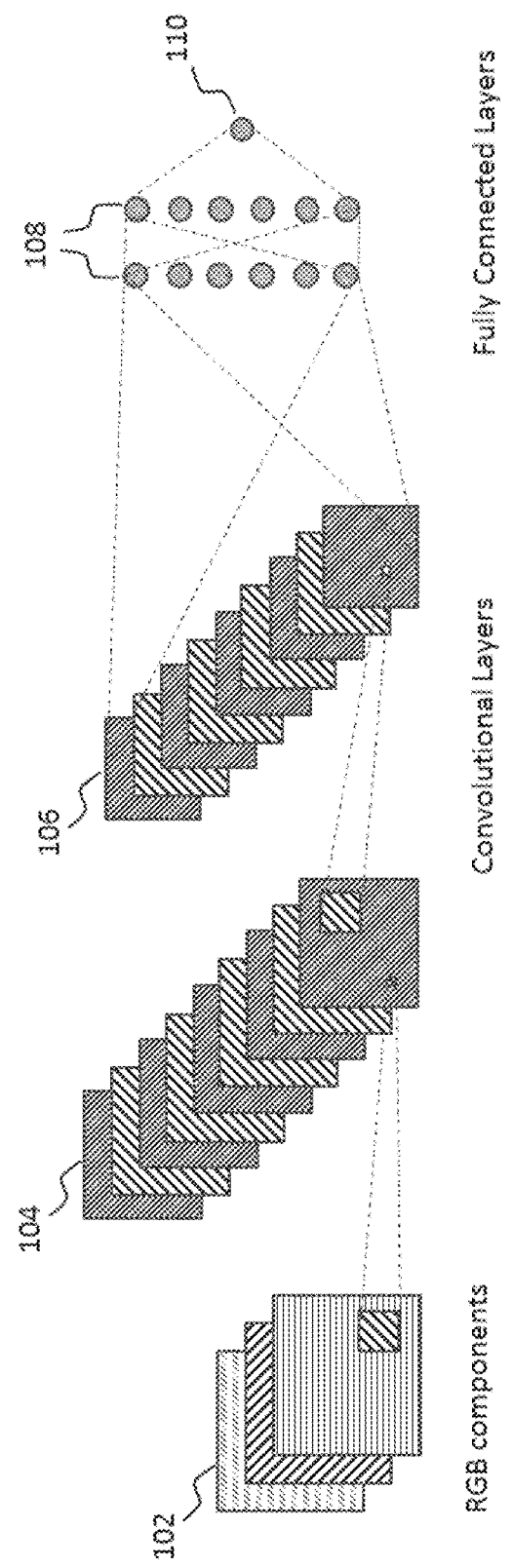
FIG. 6 shows a convolutional neural network which can be used to determine a probability value, according to some embodiments.
Figure 7:
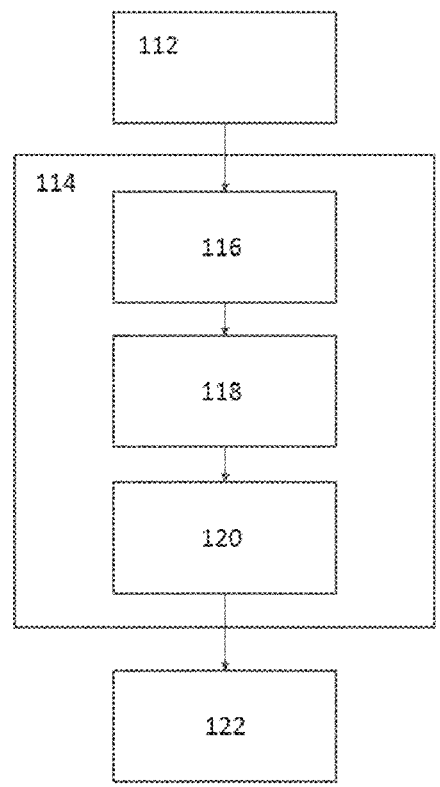
FIG. 7 shows a convolutional neural network which can be used to determine a probability value, according to some embodiments.

FIGS. 6 and 7 illustrate schematically an exemplary convolutional neural network which can be used to determine a probability value, according to some embodiments. FIG. 6 illustrates various layers within a CNN. As shown in FIG. 6, an exemplary CNN used to identify within patient data one or more characteristics of an NTRK oncogenic fusion can receive input 102 describing the red, green, and blue (RGB) components of an input histopathological image. The input 102 can be processed by multiple convolutional layers (e.g., convolutional layer 104, convolutional layer 106. The output from the multiple convolutional layers may optionally be processed by a set of fully connected layers 108 and 110. Neurons in a fully connected layer have full connections to all activations in the previous layer. The output from the fully connected layers 108 can be used to generate an output result 110 from the network. The output result can be the probability value indicating the probability of a patient suffering from cancer caused by an NTRK oncogenic fusion.

The activations within the fully connected layers 108 can be computed using matrix multiplication instead of convolution. Not all CNN implementations make use of fully connected layers. For example, in some embodiments, the convolutional layer 106 can generate output for the CNN.

In some embodiments, the convolutional layers may be sparsely connected, which differs from traditional neural network configuration found in the fully connected layers 108. Traditional neural network layers are fully connected, such that every output unit interacts with every input unit. However, the convolutional layers may be sparsely connected because the output of the convolution of a field is input (instead of the respective state value of each of the nodes in the field) to the nodes of the subsequent layer, as illustrated. The kernels associated with the convolutional layers may perform convolution operations, the output of which may be sent to the next layer. The dimensionality reduction performed within the convolutional layers is one aspect that enables the CNN to process large images.

FIG. 7 illustrates computation stages within a convolutional layer of a CNN, according to some embodiments. Input 112 to a convolutional layer 114 of a CNN can be processed in three stages of the convolutional layer 114. In some embodiments, the three stages can include a convolution stage 116, a detector stage 118, and a pooling stage 120. The convolution layer 114 can then output data to a successive convolutional layer. The final convolutional layer of the network can generate output feature map data or provide input to a fully connected layer, for example, to generate a classification or regression value.

In the convolution stage 116, the convolutional layer 114 can perform several convolutions in parallel to produce a set of linear activations. The convolution stage 116 can include an affine transformation, which is any transformation that can be specified as a linear transformation plus a translation. Affine transformations include rotations, translations, scaling, and combinations of these transformations. The convolution stage may compute the output of functions (e.g., neurons) that are connected to specific regions in the input, which can be determined as the local region associated with the neuron. The neurons may compute a dot product between the weights of the neurons and the region in the local input to which the neurons are connected. The output from the convolution stage 116 may define a set of linear activations that are processed by successive stages of the convolutional layer 114.

In some embodiments, the linear activations can be processed by a detector stage 118. In the detector stage 118, each linear activation may be processed by a non-linear activation function. The non-linear activation function increases the nonlinear properties of the overall network without affecting the receptive fields of the convolution layer. Several types of non-linear activation functions may be used. In some embodiments, the rectified linear unit (ReLU), which uses an activation function defined as f(x) =max(0, x) such that the activation is threshold at zero, may be used.

In some embodiments, the pooling stage 120 may use a pooling function that may replace the output of the convolutional layer 106 with a summary statistic of the nearby outputs. The pooling function can be used to introduce translation invariance into the neural network, such that small translations to the input do not change the pooled outputs. Invariance to local translation can be useful in scenarios where the presence of a feature in the input data is more important than the precise location of the feature. Various types of pooling functions can be used during the pooling stage 120, including max pooling, average pooling, and l2-norm pooling. In some embodiments, a CNN implementation may not include a pooling stage. In some embodiments, a CNN implementation without a pooling stage may substitute an additional convolution stage having an increased stride relative to previous convolution stages.

In some embodiments, the output from the convolutional layer 114 can then be processed by the next layer 122. In some embodiments, the next layer 122 can be an additional convolutional layer or one of the fully connected layers 108. For example, the first convolutional layer 104 of FIG. 6 can output to the second convolutional layer 106, while the second convolutional layer can output to a first layer of the fully connected layers 108.

Figure 8:
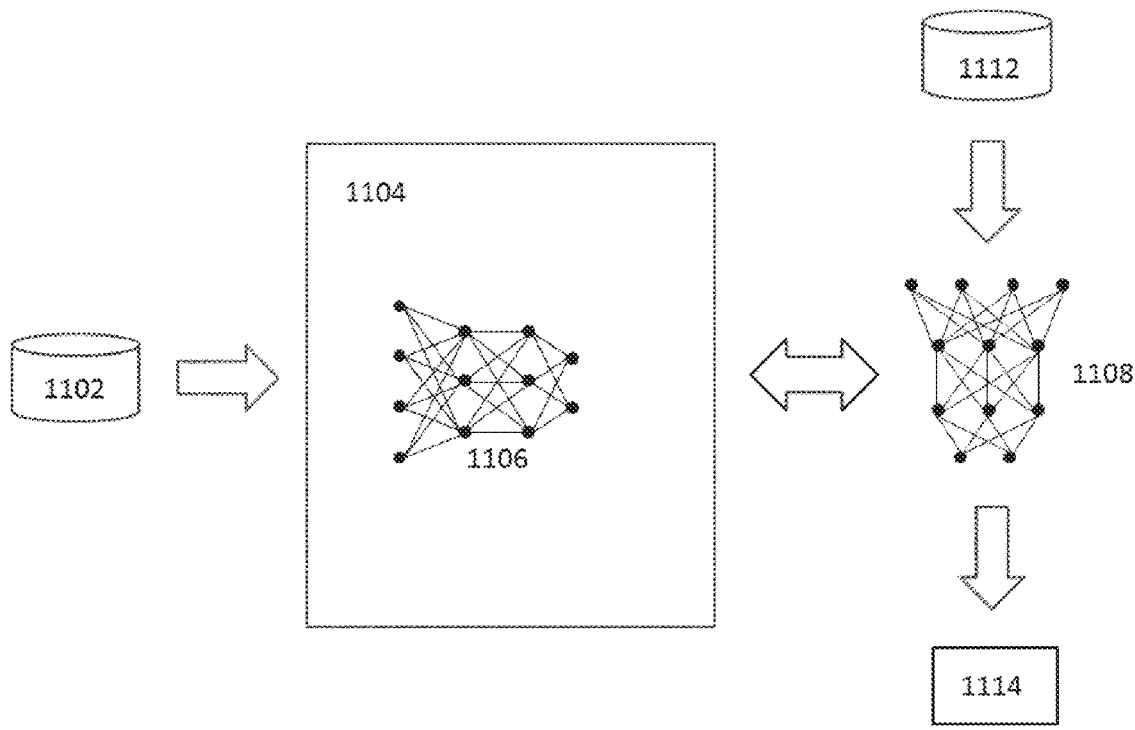
FIG. 8 shows training and deployment of a neural network, according to some embodiments.

FIG. 8 shows training and deployment of a neural network, according to some embodiments. Once a given network has been structured for a task the neural network may be trained using a training dataset 1102.

In some embodiments, to start the training process, the initial weights may be chosen randomly or by pre-training using a deep belief network. The training cycle may then be performed in either a supervised or unsupervised manner. Supervised learning is a learning method in which training is performed as a mediated operation, such as when the training dataset 1102 includes input paired with the desired output for the input, or where the training dataset includes input having known output and the output of the neural network is manually graded. The network may process the inputs and compare the resulting outputs against a set of expected or desired outputs. Errors are then propagated back through the system. The training framework 1104 may adjust the weights that control the untrained neural network 1106. The training framework 1104 may provide tools to monitor how well the untrained neural network 1106 is converging towards a model suitable to generating correct answers based on known input data. The training process may occur repeatedly as the weights of the network are adjusted to refine the output generated by the neural network. The training process can continue until the neural network reaches a statistically desired accuracy associated with a trained neural network 1108. The trained neural network 1108 can then be deployed to implement any number of machine learning operations. A new set of patient data 1112 can be inputted into the trained neural network 1108 to determine a probability value, the probability value indicating the probability of a patient suffering from cancer caused by a mutation of a neurotrophic receptor tyrosine kinase (NTRK) gene.

Figure 9:
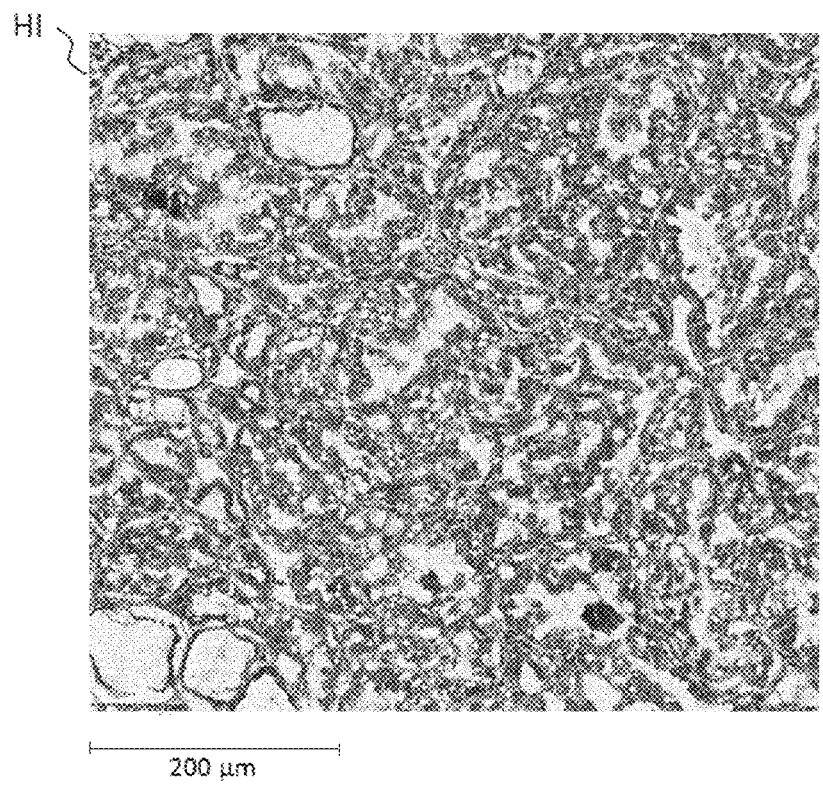
FIG. 9 shows a histopathological image (HI) of tumor tissue of a patient suffering from cancer.

FIG. 9 is an example of a histopathological image (HI) of tumor tissue of a patient suffering from cancer.

Figure 10:
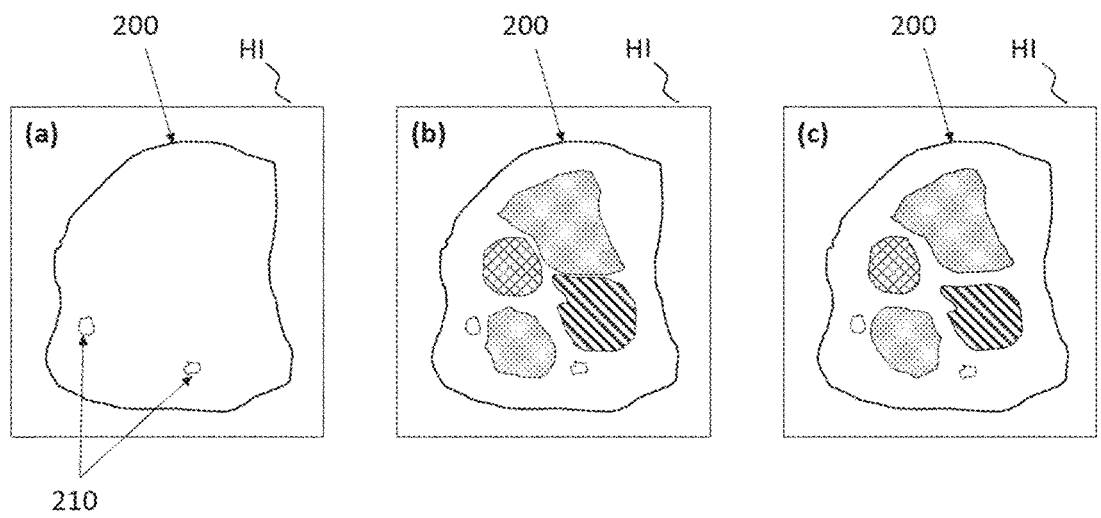
FIG. 10 (a) illustrates a digital image of an HE stained, formalin-fixed, paraffin-embedded (FFPE) tumor tissue section.

FIG. 10 illustrates of the performance of the prediction model and an example of the way to represent its output, according to some embodiments.

FIG. 10 (a) illustrates a digital image of an HE stained, formalin-fixed, paraffin-embedded (FFPE) tumor tissue section. As shown, the tissue 200 contains holes 210. Such an image may serve as input to the prediction model. Note that the details of the tissue revealed by the HE stain (which result in different colors and intensities with in the tissue section) are omitted for clarity. However, these reveal to the trained person only the position, shape, and thus type of cells, not their molecular composition.

FIG. 10 (b) illustrates an output example of the prediction tool. As shown, a digital image is generated corresponding to the layout of the tissue scan in FIG. 10 (a). The tissue scan is usually overlaid by a pseudo-colored image in which the color or the intensity of a color corresponds to the probability that an area of the tissue shows a tumor cancer caused by an NTRK oncogenic fusion (here only black/white images are shown). In a preferred embodiment, the colors are chosen to represent the typical colors (eg brownish or redish) of immunohistochemistry dyes to generate a 'pseudo IHC image'. Colors are indicated in the figure by areas which are dotted (indicating a predicted weak staining intensity), cross hatched (moderately stained), or thickly hatched (strongly stained).

FIG. 10 (c) illustrates a digital image of an adjacent FFPE tumor tissue section stained with an antibody for indicating presence of TRK proteins using immunohistochemistry. Note that the digital image corresponds very well to the predictions made by the prediction model as shown in FIG. 10 (b), even though the molecular assay was conducted on an adjacent tissue section.

Note that this performance holds true at higher magnification as well, when zooming in from the tissue to the morphology/cellular level. In a preferred embodiment, predicted images such as shown in FIG. 10 (b) turn from HE colors to pseudo IHC colors in (almost) real time when zooming in to one zone or moving across the tissue. This is enabled by edge analysis, and enables the system according to the present invention to process information locally and respond more quickly to situations. This feature also allows our tool to work in telepathology settings, even in mobile computing devices such as smartphones. In a preferred embodiment, the prediction model is embedded in a website for convenient installation on routine computer devices.

IHC can be performed for example with the research use only panTRK monoclonal antibody EPR17341 (Abcam, Cambridge, MA), see Hechtman et al., The American Journal of Surgical Pathology (2017), 41 (11), 1547-1551, PMID 28719467, using for example a Ventana Autostainer Discovery Ultra equipment.

Figure 11:
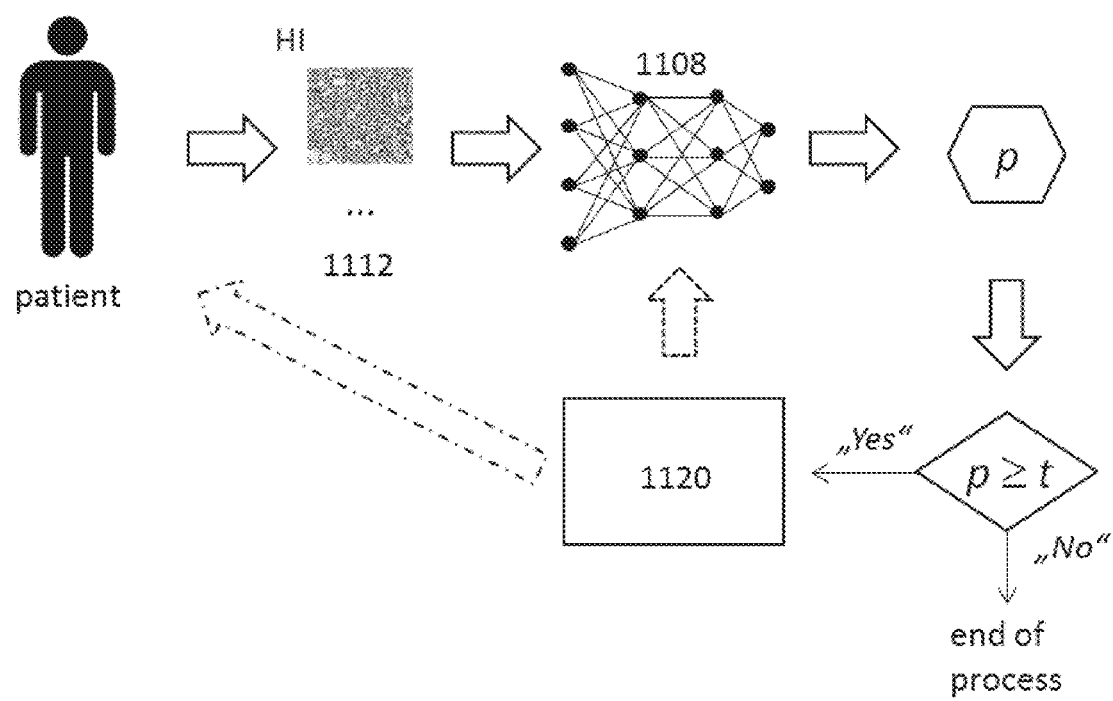
FIG. 11 shows schematically a process for determining a probability value in practice, according to some embodiments.

FIG. 11 shows a process for using the present invention in practice, according to some embodiments. The starting point of the process is a patient suffering from cancer. One aim of the process may be to find out whether the cancer is caused by a mutation of a neurotrophic receptor tyrosine kinase (NTRK) gene. In a first step, patient data 1112 may be collected/retrieved. The patient data 1112 may comprise at least one histopathological image (HI) of tumor tissue of the patient. In a following step, the patient data may be inputted into a prediction model 1108 which is trained by supervised learning. For the supervised training, patient data of a multitude of patients can be used for whom it has been determined whether they suffer from cancer caused by a mutation of a neurotrophic receptor tyrosine kinase (NTRK) gene or whether they suffer from cancer not caused by a mutation of a neurotrophic receptor tyrosine kinase (NTRK) gene.

In some embodiments, trained prediction model 1108 may be configured to determine a probability value p from the inputted patient data 1112. The probability value may indicates the probability of the patient suffering from cancer caused by a mutation of a neurotrophic receptor tyrosine kinase (NTRK) gene.

In a further step, the probability value p may be compared with a predefined threshold value t.

In some embodiments, if the probability value p is smaller than the predefined threshold value t (p≥t: "No"), then it may be unlikely that the patient suffers from cancer caused by a mutation of a neurotrophic receptor tyrosine kinase (NTRK) gene. Other causes for the cancer may have to be identified; as such, the process ends.

In some embodiments, if the probability value p is equal to or greater than the predefined threshold value t (p≥t: "Yes"), then it may be likely that the patient suffers from cancer caused by a mutation of a neurotrophic receptor tyrosine kinase (NTRK) gene. A subsequent step 1120 may be initiated. In some embodiments, further investigations may be initiated in order to verify that the cancer is caused by a mutation of a neurotrophic receptor tyrosine kinase (NTRK) gene. This can be done e.g. by a genetic analysis of the tumor tissue. The results of the further investigations can be used to optimize (further supervised learning) the prediction model 1108. If the further investigation verifies that the cancer is caused by a mutation of a neurotrophic receptor tyrosine kinase (NTRK) gene, the patient can be treated with a Trk inhibitor. In some embodiments, the likelihood of the cancer being caused by a mutation of a neurotrophic receptor tyrosine kinase (NTRK) gene may be considered to be so high that the patient is treated directly (without any further genetic analysis of the tumor tissue) with a Trk inhibitor.

Figure 12:
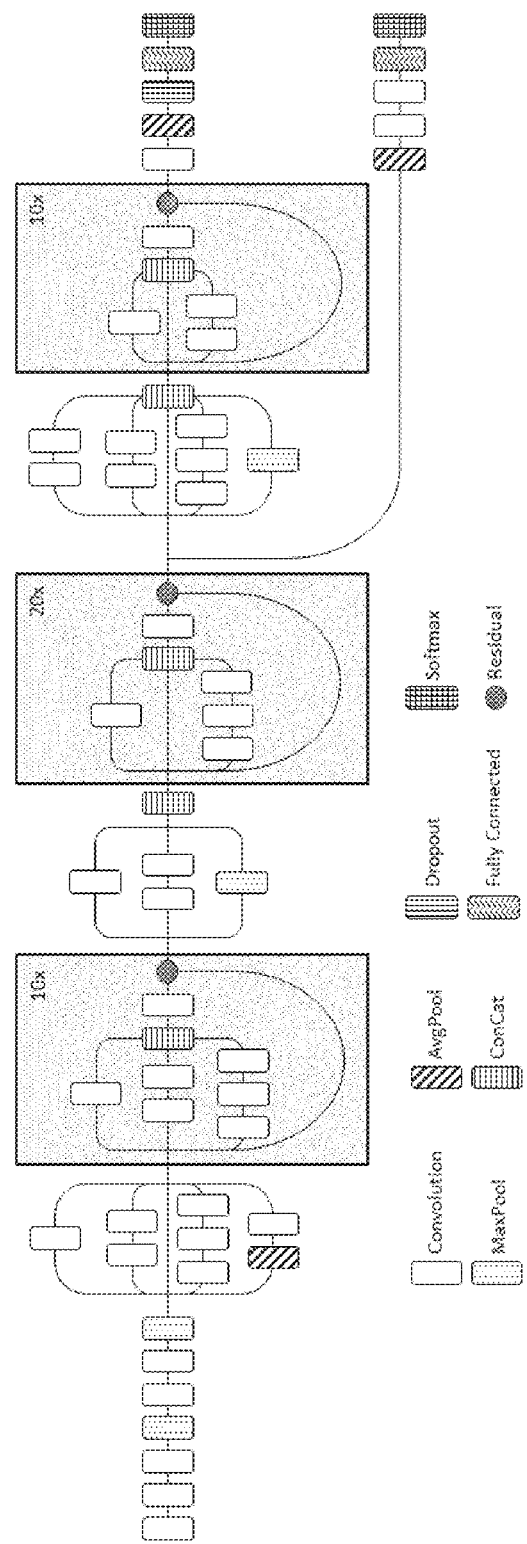
FIG. 12 shows the layer structure of the artificial neural network, according to some embodiments.
Figure 13:
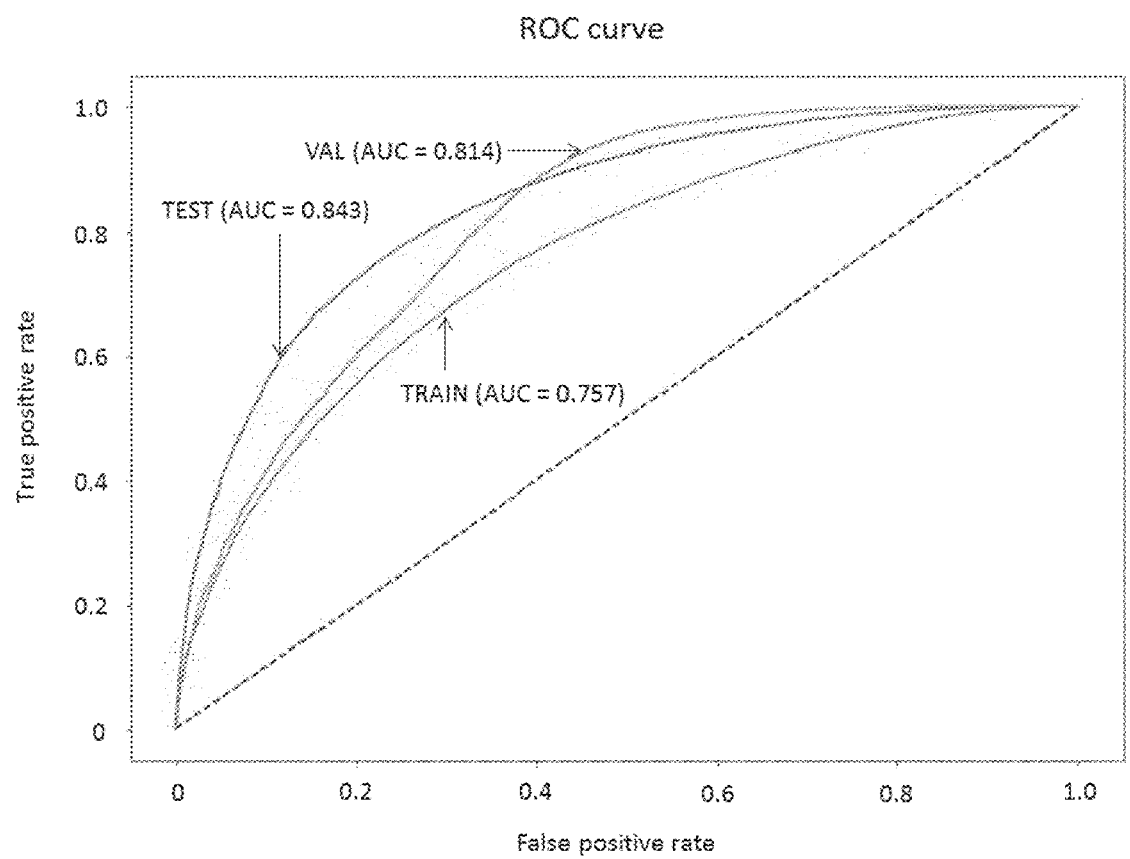
FIG. 13 shows a receiver operating characteristic curve (ROC curve), according to some embodiments.
Figure 14:
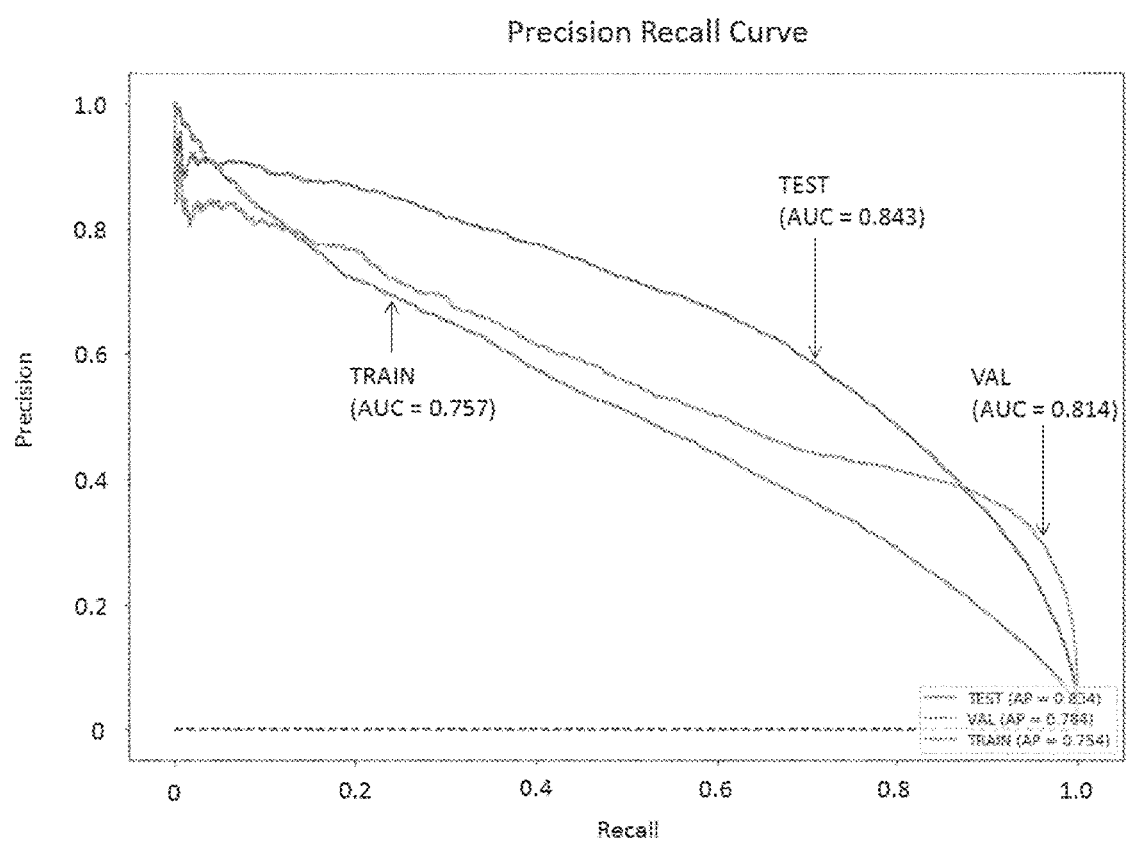
FIG. 14 a precision recall curve, according to some embodiments.

FIGS. 12 to 14 illustrate an artificial neural network was set up for the prediction of probability values, each probability value indicating the probability of a subject patient suffering from cancer of the thyroid gland caused by an NTRK oncogenic fusion.

FIG. 12 shows the layer structure of the artificial neural network, according to some embodiments. The network is provided by IBM under the name Inception ResNet v2 (https://developer.ibm.com/exchanges/models/all/max-inception-resnet-v2/). The network pre-trained on ImageNet was used with transfer learning (in Keras+Tensorflow).

The data sets for training and verification were taken from The Cancer Genome Atlas (TCGA: https://portal.gdc.cancer.gov/). Further data were obtained from Auria, the biobank of Turku University Hospital, Finland.

Digital images in .svs format of HE stained tissues sections (cryo and or FFPE formalin fixed paraffin embedded) were used as histopathological images. The age of the patient at diagnosis was also used as input parameter for prediction. Information extracted from the whole exome sequencing data available TCGA on the mutational status of key oncogenes were used as well as NGS panel results (Illumina TST 170) on the Auria samples.

FIG. 13 shows the results in the form of a receiver operating characteristic curve (ROC curve). TRAIN refers to the training data set, VAL refers to the validation data set and TEST refers to the testing data set. The training data set was used to train the prediction model, the validation data set was used to validate the prediction model and the testing data set was used for prediction purposes. AUC means area under the curve.

FIG. 14 shows the result in the form of a precision recall curve. TRAIN refers to the training data set, VAL refers to the validation data set and TEST refers to the testing data set. The training data set was used to train the prediction model, the validation data set was used to validate the prediction model and the testing data set was used for prediction purposes. AUC means area under the curve.

The invention claimed is:

1. A computer-implemented method for identifying one or more candidate signs indicative of an NTRK oncogenic fusion within patient data associated with a subject patient, the method comprising:
   receiving historical patient data for which one or more candidate signs indicative of an NTRK oncogenic fusion have been verified or excluded, the historical patient data comprising a plurality of histopathological images of tumor tissue;
   training a prediction model via machine learning to predict a probability of cancer caused by the NTRK oncogenic fusion for each histological image of the plurality of histopathological images, thereby obtaining a trained prediction model;
   receiving patient data of a subject patient suffering from cancer, the patient data comprising at least one histopathological image of tumor tissue of the subject patient;
   inputting the patient data into the trained prediction model, the trained prediction model being configured for identifying within the patient data one or more characteristics of an NTRK oncogenic fusion;
   receiving as an output from the trained prediction model a probability value, the probability value indicating the probability of the subject patient suffering from cancer caused by an NTRK oncogenic fusion;
   comparing the probability value with a predefined threshold value; and
   in the event that the probability value is equal to or greater than the threshold value: initiating further investigations for verification of the indication that the subject patient suffers from cancer caused by an NTRK oncogenic fusion.

2. A system, comprising:
   a processor; and
   a memory storing an application program configured to perform, when executed by the processor, an operation for identifying one or more candidate signs indicative of an NTRK oncogenic fusion within patient data associated with a subject patient, the operation comprising:
   receiving historical patient data for which the one or more candidate signs indicative of the NTRK oncogenic fusion have been verified or excluded, the historical patient data comprising a plurality of histopathological images of tumor tissue;
   training a prediction model via machine learning to predict a probability of cancer caused by the NTRK oncogenic fusion for each histological image of the plurality of histopathological images, thereby obtaining a trained prediction model;
   receiving patient data of a subject patient suffering from cancer, the patient data comprising at least one histopathological image of tumor tissue of the subject patient;
   inputting the patient data into the trained prediction model, the trained prediction model being configured for identifying within the patient data one or more characteristics of an NTRK oncogenic fusion;
   receiving as an output from the trained prediction model a probability value, the probability value indicating the probability of the subject patient suffering from cancer caused by an NTRK oncogenic fusion;

comparing the probability value with a predefined threshold value; and in the event that the probability value is equal to or greater than the threshold value: initiating further investigations for verification of the indication that the subject patient suffers from cancer caused by an NTRK oncogenic fusion.

3. A non-transitory computer-readable storage medium comprising processor-executable instructions with which to perform an operation for identifying one or more candidate signs indicative of an NTRK oncogenic fusion within patient data associated with a subject patient, the operation comprising:

receiving historical patient data for which one or more candidate signs indicative of an NTRK oncogenic fusion have been verified or excluded, the historical patient data comprising a plurality of histopathological images of tumor tissue;

training a prediction model via machine learning to predict a probability of cancer caused by the NTRK oncogenic fusion for each histological image of the plurality of histopathological images, thereby obtaining a trained prediction model;

receiving patient data of a subject patient suffering from cancer, the patient data comprising at least one histopathological image of tumor tissue of the subject patient;

inputting the patient data into the trained prediction model, the trained prediction model being configured for identifying within the patient data one or more characteristics of an NTRK oncogenic fusion;

receiving as an output from the trained prediction model a probability value, the probability value indicating the probability of the subject patient suffering from cancer caused by an NTRK oncogenic fusion;

comparing the probability value with a predefined threshold value; and in the event that the probability value is equal to or greater than the threshold value: initiating further investigations for verification of the indication that the subject patient suffers from cancer caused by an NTRK oncogenic fusion.

* * * * *